United States Patent
Li et al.

(10) Patent No.: US 9,607,405 B2
(45) Date of Patent: Mar. 28, 2017

(54) METHOD AND DEVICE FOR DETECTING DISPLACEMENT IN ELASTOGRAPHY

(75) Inventors: Shuangshuang Li, Shenzhen (CN); Rui Fan, Shenzhen (CN)

(73) Assignee: SHENZHEN MINDRAY BIO-MEDICAL ELECTRONICS CO., LTD., Shenzhen (CN)

(*) Notice: Subject to any disclaimer, the term of this patent is extended or adjusted under 35 U.S.C. 154(b) by 576 days.

(21) Appl. No.: 14/126,222

(22) PCT Filed: Mar. 27, 2012

(86) PCT No.: PCT/CN2012/073135
§ 371 (c)(1),
(2), (4) Date: May 6, 2014

(87) PCT Pub. No.: WO2012/171388
PCT Pub. Date: Dec. 20, 2012

(65) Prior Publication Data
US 2014/0254869 A1    Sep. 11, 2014

(30) Foreign Application Priority Data
Jun. 14, 2011 (CN) .......................... 2011 1 0159194

(51) Int. Cl.
*A61B 8/08* (2006.01)
*G06T 7/60* (2017.01)
(Continued)

(52) U.S. Cl.
CPC ................ *G06T 7/60* (2013.01); *A61B 8/485* (2013.01); *G01N 29/0654* (2013.01);
(Continued)

(58) Field of Classification Search
None
See application file for complete search history.

(56) References Cited

U.S. PATENT DOCUMENTS 5,495,771 A * 3/1996 Sumi .................. A61B 8/485
73/573

2008/0119732 A1 * 5/2008 Hiltawsky ............. A61B 8/485
600/438
(Continued)

FOREIGN PATENT DOCUMENTS

| CN | 1586408 A | 3/2005 |
|----|-----------|--------|
| CN | 1964670 A | 5/2007 |

(Continued)

OTHER PUBLICATIONS

Lindop, Joel E., Graham M. Treece, Andrew H. Gee, and Richard W. Prager. "Phase-based ultrasonic deformation estimation." IEEE transactions on ultrasonics, ferroelectrics, and frequency control 55, No. 1 (2008): 94-111.*

(Continued)

*Primary Examiner* — Sumati Lefkowitz
*Assistant Examiner* — Carol Wang
(74) *Attorney, Agent, or Firm* — Kory D. Christensen; Stoel Rives LLP

(57) ABSTRACT

Disclosed are a method and a device for detecting displacement in elastography. The method comprises: acquiring a target point, acquiring a cross-correlation phase calculation location of the target point in a second frame image; calculating a cross-correlation phase according to the cross-correlation phase calculation location; calculating a longitudinal displacement result according to the cross-correlation phase; and calculating a gradient of the displacement result to obtain a strain result. Through the elastography method and device, I/Q-channel echo baseband signals, obtained by downsampling, of two frames before and after compression are acquired, displace information between the two frames is rapidly detected by guiding phase estimation, and axial gradient calculation is performed to obtain strain information, which can not only obtain a strain image of high quality but also reduce the calculation amount, thereby satisfying the clinical real-time requirement.

7 Claims, 2 Drawing Sheets

(51) Int. Cl.
   *G01N 29/06*   (2006.01)
   *G01S 7/52*    (2006.01)
   *G06T 7/00*    (2017.01)
(52) U.S. Cl.
   CPC ...... *G01S 7/52017* (2013.01); *G01S 7/52042* (2013.01); *G06T 7/0012* (2013.01); *G01N 2291/02475* (2013.01); *G01N 2291/02827* (2013.01)

(56) References Cited

U.S. PATENT DOCUMENTS

2009/0247871 A1  10/2009  Varghese et al.
2010/0106018 A1   4/2010  Jiang et al.

FOREIGN PATENT DOCUMENTS

CN   101530333 A       9/2009
EP     1746385 A1 *    1/2007   ........... G01B 11/002
JP   2004057652 A *    2/2004

OTHER PUBLICATIONS

Pinton, Gianmarco F., Jeremy J. Dahl, and Gregg E. Trahey. "Rapid tracking of small displacements with ultrasound." IEEE transactions on ultrasonics, ferroelectrics, and frequency control 53, No. 6 (2006): 1103-1117.*
Translated Version of JP 2004-057652.*

* cited by examiner

METHOD AND DEVICE FOR DETECTING DISPLACEMENT IN ELASTOGRAPHY

TECHNICAL FIELD

The disclosure relates to elastography, in particular to methods and devices for detecting displacement in elastography.

BACKGROUND

Ultrasound elastography is an important method for assisting cancer detection, in particular mammary cancer detection, in B mode ultrasound images, which is widely used in clinic. Ultrasound elastography mainly acquires ultrasound echoes from target tissues by ultrasound imaging, detects information about tissue elasticity using particular algorithms, and visually displays the information in the form of images, so as to assist doctors to make a diagnosis or therapy.

Conventional ultrasound elastography acquires two frames of ultrasound echo signals in succession by slightly compressing the tissue using a probe or with the assistance of a patient's breathing or vascular pulsation process, etc., and then determines the displacement (which is the change of the spatial location of the target tissue at two different times) between the two signal frames by particular displacement detection methods. Then, the axial strain of the tissue can be calculated from the axial gradient of the displacement. This axial strain may represent the elasticity of the tissue. Under the same external compressive force, the larger the strain, the softer the tissue; the smaller the strain, the harder the tissue. The strain of a target tissue may be displayed in the form of images, which can visually show the difference of hardness or elasticity between different tissues. These images are called strain images. This method is also referred to as strain imaging.

In the process described above, the contrast-to-noise ratio (CNR) of the resulting strain images, whether it may be achieved in real time, and whether the frame rate can meet clinical needs, etc. may be affected by whether the displacement can be correctly detected and whether the calculation can be done rapidly. Conventional methods for detecting displacement are usually categorized into three categories: the time domain detection methods based on cross-correlation, the methods based on phase shift, and the methods based on tissue Doppler imaging (TDI). The methods based on cross-correlation may obtain images with good quality, but often require a large amount of calculation and particular echo data sampling rate. The methods based on phase shift can be fast, but there may be phase aliasing, so they can be more suitable for the situations with small displacements and may generally ignore the lateral displacement, and can result relatively poor image quality. The methods based on TDI can be easily implemented, but may depend on the signal-to-noise ratio (SNR) of the Doppler signals and on the processing methods, and may still have phase aliasing and also ignore the lateral displacement and have relatively poor image quality.

SUMMARY

The present disclosure provides methods and devices for detecting displacement in elastography which can reduce the amount of calculation during the imaging process.

In some embodiments, a method for detecting displacement in elastography is provided that may include:

selecting a target point;
obtaining a cross-correlation phase calculation location of the target point in a second frame image;
calculating a cross-correlation phase based on the cross-correlation phase calculation location;
calculating a longitudinal displacement based on the cross-correlation phase; and
obtaining a strain by calculating a gradient of the displacement.

In some embodiments, a device for detecting displacement in elastography is provided that may include:
a target point selection apparatus that can select a target point;
a search apparatus that can obtain a cross-correlation phase calculation location of the target point in a second frame image;
a cross-correlation phase calculation apparatus that can calculate a cross-correlation phase based on the cross-correlation phase calculation location;
a longitudinal displacement calculation apparatus that can calculate a longitudinal displacement based on the cross-correlation phase; and
a strain calculation apparatus that can determine a strain by calculating a gradient of the displacement.

The methods and devices described herein may be provided by embodiments of present disclosure. By acquiring two frames of down-sampled I/Q baseband echo signals before and after compression and rapidly determining the displacement between the two frames using guided phase estimation and then obtaining the strain by calculating the axial gradient, the methods and devices described herein may not only provide strain images with high quality but also reduce the amount of calculation, thereby meeting clinical requirements in real time.

DETAILED DESCRIPTION

The present disclosure will be described by way of specific embodiments with reference to drawings.

Figure 1:
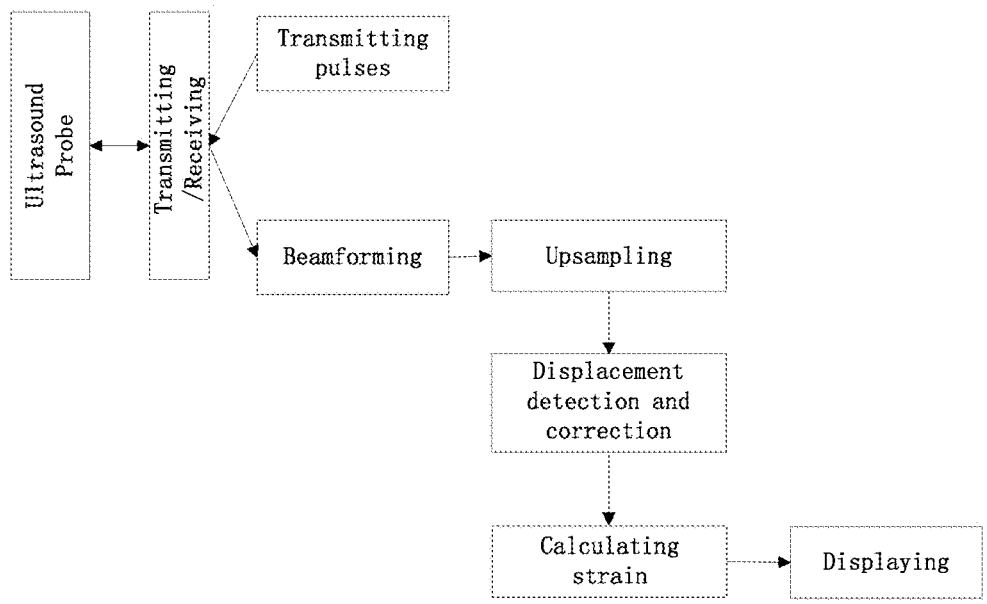
FIG. 1 is a schematic showing an elastography system according to an embodiment of the present disclosure.

FIG. 1 is a schematic of an elastography system according to one embodiment of the present disclosure. When elastography is performed, an ultrasound probe may transmit ultrasound waves and receive echoes according to predetermined scanning rules and output radio frequency (RF) signals after beamforming. The RF signals can be quadraturely demodulated to generate I (in-phase)/Q (quadrature) baseband signals. At the same time, down-sampling may be performed to reduce the sampling rate of the I/Q signals, where the rate of the down-sampling may be pre-set by the system. Then, the displacement may be detected based on the guided phase zero estimation (GPZE) algorithm. Each time a pair of I/Q signal frames may be used to calculate one frame of displacement. Then, the strain may be calculated based on the displacement. The strain may then be corrected and/or smoothed, etc. by post processing. Finally, a strain image can be displayed.

The GPZE algorithm utilize guided searching to more quickly and correctly detect the phase of the cross-correlation function between two successive frames, derives the relationship between the phase and the longitudinal displacement, and calculates the longitudinal displacement between the two frames. The algorithm can significantly reduce the amount of calculation while ensuring good quality of the displacement estimation. In addition, the scope of the displacement detection may be expanded. The GPZE algorithm can be suitable for both small- and large-displacement cases.

Assume that two successive frame signals can be represented as:

$$f_u(t, x) = A_u(t, x)e^{j(\omega_c t+\theta)}$$

$$f_c(t, x) = A_c(t-u_y, x-u_x)e^{j[\omega_c(t-u_y)+\theta]} = A_c(t-u_y, x-u_x)e^{j[\omega_c(t-\frac{nT_c}{2}-\tau)+\theta]},$$

where $\omega_c$ is the center frequency of the signals, $\theta$ is an initial phase of the signals, $T_c$ is the period of the signals, which corresponds to the center frequency $\omega_c$, $u_x$ is the spatial lateral offset caused by compression, and $u_y$ is the longitudinal offset caused by compression. $u_y$ may be expressed as $u_y=\tau+nT_c/2$, where n is an integer, and $\tau$ is in the range of $-T_c/2 \sim T_c/2$.

The signals can be quadraturely demodulated into baseband signals. The complex form for the baseband signals may be represented as:

$$f_{ub}(t,x)=A_u(t,x)e^{j\theta}$$

$$f_{cb}(t,x)=A_c(t-u_y,x-u_x)e^{j(-\omega_c\tau-\omega_c nT_c/2+\theta)}.$$

Then, the cross-correlation function between the baseband signals may be expressed as:

$$R_b(u_0, x_0) = \int_{t_0-\Delta t}^{t_0-\Delta t} f_{ub}(t, x) \cdot f_{cb}^*(t+u_0, x+x_0) dt$$

$$= \int_{t_0-\Delta t}^{t_0-\Delta t} A_u(t, x)e^{j\theta} \cdot A_c(t-u_y+u_0, x-u_x+x_0)e^{-j[\omega_c(-nT_c/2-\tau)+\theta]} dt$$

$$= e^{jn\pi}\left(\int_{t_0-\Delta t}^{t_0-\Delta t} A_u(t, x) \cdot A_c(t-u_y+u_0, x-u_x+x_0) dt\right)e^{j\omega_c\tau}$$

$$= e^{jn\pi} R_{eb}(u_0, x_0)e^{j\omega_c\tau},$$

where $u_0$ and $x_0$ respectively represent the longitudinal and lateral offsets between the two target data frames when calculating the cross-correlation function, and $R_{eb}$ is the cross-correlation function between the envelope signals of the two data frames.

Multiplying both sides of the equation above by $e^{-jn\pi}$ may result:

$$R'(u_0, x_0) = R_b(u_0, x_0)e^{-jn\pi}$$

$$= (-1)^n R_b(u_0, x_0)$$

$$= R_{eb}(u_0, x_0)e^{j\omega_c\tau}.$$

The longitudinal offset and the lateral offset between the envelope data of the two frames may be obtained by finding $u_0$ and $x_0$ that give rise to a maximum for the envelope cross-correlation function $R_{eb}(u_0,x_0)$. The cross-correlation function $R_b(u_0,x_0)$ may then be calculated using the baseband data of the corresponding offset locations of the two successive frames. Because the difference between the cross-correlation function and the R' function is only $(-1)^n$, the cross-correlation phase may be calculated by $\phi=\omega_c\tau$. Finally, the time shift or the longitudinal displacement between the two signal frames may be represented as:

$$u_y=nT_c/2+\tau=nT_c/2\phi/\omega_c.$$

It should be noted that, since the time shift (whose unit is time) and the longitudinal displacement (whose unit is length) have one-to-one correspondence, the present disclosure uses the terms "longitudinal displacement" and "time shift" interchangeably.

A method for detecting displacement in elastography is provided herein that can include:
selecting a target point;
obtaining a cross-correlation phase calculation location of the target point in a second frame image;
calculating a cross-correlation phase based on the cross-correlation phase calculation location;
calculating a longitudinal displacement based on the cross-correlation phase.

In an embodiment, baseband signal data may be obtained before selecting the target point. The baseband signal data may be gridized, where the nodes of the grid may serve as displacement estimation points. The target points may be selected from the displacement estimation points.

Figure 4:
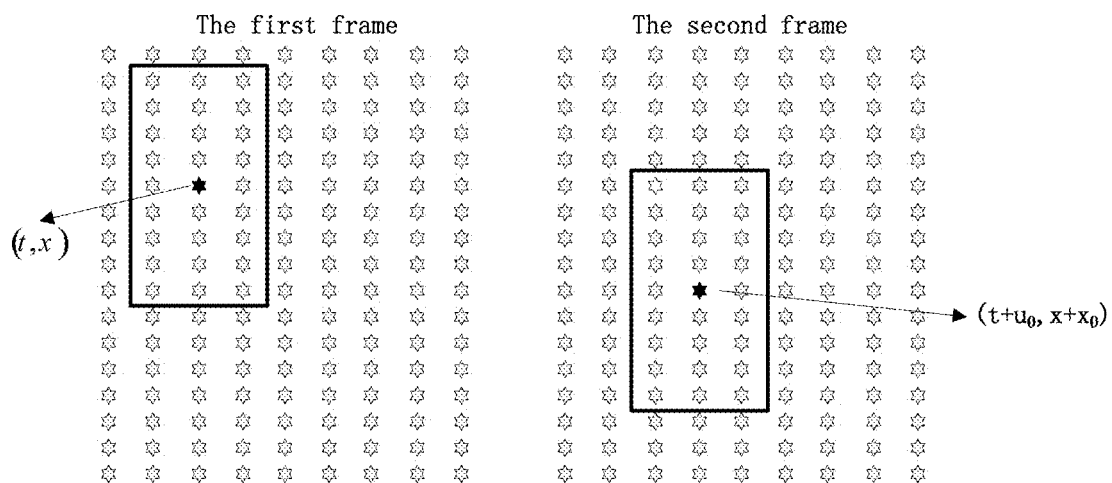
FIG. 4 is a schematic showing displacement searching according to an embodiment of the present disclosure.

In some embodiments below, during some of the calculation, a block of data which centers on (or is referenced on) a location may be selected for calculation, as shown in FIG. 4. The size of the block of data may be pre-set by the system. These data block used in calculation are referred to as kernel, which may be one-dimensional or two-dimensional.

In an embodiment, obtaining the cross-correlation phase calculation location of the target point in the second frame image may include obtaining the longitudinal location for cross-correlation phase calculation data. For example, obtaining the cross-correlation phase calculation location of the target point in second frame image may include: obtaining a longitudinal displacement of a previous calculation point of the target point; in the second frame image, within a region that centers on the sum of the location of the target point and the longitudinal displacement of the previous calculation point, searching a point whose correlation with a kernel data is maximum. The longitudinal location of this point can be the longitudinal location for the cross-correlation phase calculation of the target point in the second frame image.

In an embodiment, obtaining the cross-correlation phase calculation location of the target point in the second frame image may further include obtaining the horizontal location for cross-correlation phase calculation data. For example, obtaining the cross-correlation phase calculation location of the target point in second frame image may include: laterally searching a point at which data correlation is maximum in the vicinity of the longitudinal location for the cross-correlation phase calculation. The horizontal location of this point can be the horizontal location for the cross-correlation phase calculation data.

In an embodiment, laterally searching the point at which the data correlation is maximum in the vicinity of the longitudinal location for the cross-correlation phase calculation may be performed once every few points.

In another embodiment, obtaining the cross-correlation phase calculation location of the target point in the second frame image may include obtaining both longitudinal and horizontal locations for cross-correlation phase calculation data. For example, obtaining the cross-correlation phase calculation location of the target point in the second frame image may include:

in the second frame image, using the target point as center, within a pre-set lateral search region, searching a point at which the cross-correlation between the envelope data of the two frames is maximum. The horizontal location of this point can be the horizontal location for the cross-correlation phase calculation;

in the second frame image, within a region which centers on the sum of the location of the target point and the longitudinal displacement of the previous calculation point of the target point, searching a point whose correlation with the kernel data is maximum. The longitudinal location of this point can be the longitudinal location for the cross-correlation phase calculation.

Figure 2:
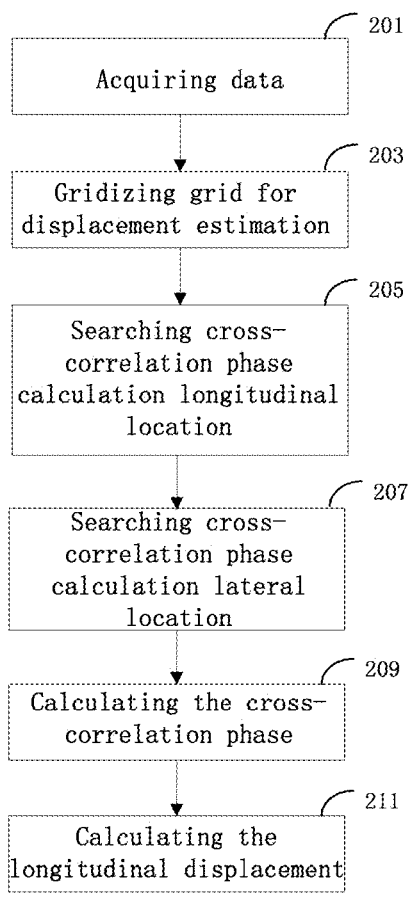
FIG. 2 is a flow chart of a method for detecting displacement in elastography according to an embodiment of the present disclosure.

FIG. 2 is a flow chart of a method for detecting displacement in elastography according to an embodiment of the present disclosure. The method may include:

201, acquiring data;

in some embodiments, acquiring a pair of I/Q baseband signal frame data.

Each frame of displacement data may be calculated using two frames of I/O baseband signal data, where the displacement data can represent the spatial relative displacement between two frames of signals. The two frames of baseband signal data may be two successive frames of data or two frames of data with certain frame interval, where the frame interval may be pre-set by the imaging system. Using two frames of data with certain frame interval, the amount of displacement between the two data frames can be effectively adjusted, thereby improving the quality of resulting strain images.

Each frame of the baseband signal data can include I data and Q data. The sampling rate of the baseband signal may be different from that of the RF data, and the down-sampling rate may be pre-set by the imaging system. The larger the down-sampling rate, the smaller the amount of subsequent calculation, but the quality of the displacement estimation and the spatial resolution of the resulting images may be affected.

After I data and Q data are acquired, their envelope data may be calculated. The envelope data may be used for calculating the offset of the envelope as described below. Calculating the envelope may be performed for each sampling point of the I/Q data, where the envelope data at sampling point i may be calculated as follows:

$$envelop(i)=\sqrt{I^2(i)+Q^2(i)}.$$

203, forming a grid for displacement estimation;

Since the sampling rate of the baseband signal is still relatively high while the displacements are generally small, the difference between the displacements of adjacent sampling points can be very small. Therefore, it may not be necessary to estimate the displacement for each sampling point of the baseband signal data. Pre-setting the locations of displacement estimation points can effectively eliminate or reduce redundant calculation.

Figure 3:
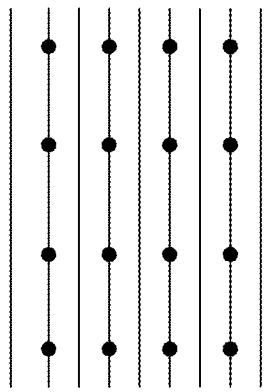
FIG. 3 is a schematic showing gridization of frame data according to an embodiment of the present disclosure.

FIG. 3 is a schematic of gridization of frame data according to an embodiment of the present disclosure, in which the black points (i.e., the nodes of the grid) are possible locations where the displacement may be estimated, and the black lines represent baseband signal data or envelope data. The gridization is based on the locations of the sampling points of the first frame of the two signal frames.

In longitudinal direction, starting from the data with lowest depth, points at which displacement is estimated may be selected at longitudinal intervals of every few sampling points (or every certain depth). The longitudinal intervals may be pre-set by the imaging system.

In lateral direction, starting from the scanning line at the center of the probe, points at which displacement is estimated may be selected at lateral intervals of every few sampling lines (or every certain width). The lateral intervals may be pre-set by the imaging system.

In the present disclosure, the offset search, the phase-shift detection, the displacement calculation, and the strain estimation may be performed at the nodes (i.e., the displacement estimation points) of the grid described above.

After the grid is formed, the amount of calculation for obtaining strain images may be significantly reduced, especially when the lateral and longitudinal intervals are very large. However, if the intervals were too large, the quality of the images may be affected, as well as the result of the displacement estimation and the spatial resolution of the images.

205, searching the longitudinal location for cross-correlation phase calculation data;

In order to obtain cross-correlation phase calculation location, the longitudinal location for the cross-correlation phase calculation of the target point in the second frame image may be found, that is, determining the longitudinal offset for the cross-correlation phase calculation data, or the longitudinal offset at which the envelope cross-correlation function between the two data frames is maximum.

The longitudinal offset may be obtained by searching the envelope data based on block-matching. During each search, one of the grid nodes in the first frame of the envelope data may be chosen as the target point. Using this target point as a center, the kernel data may be selected. Then, along the longitudinal direction, the location at which the correlation with the kernel data is maximum may be searched in the second data frame. The offset between this location and the target point is the longitudinal offset. Methods for finding the location with maximum correlation may be the SAD method or the NCC method, etc. The location at which the SAD is minimum or the NCC is maximum can be the location with maximum correlation. Other suitable methods may be used.

When searching the longitudinal offset, on the base of block-matching, guided searching may be used according to an embodiment of present disclosure to increase the speed of the calculation. After the user select the region of interest (ROI), the guided searching may be implemented by two different methods. The difference between the two methods is that the depth from which the calculation start are different, thereby the amount of calculation are also different.

According to the first method, whatever the depth of the ROI selected by the user is, the calculation may start from the data at the surface of the probe (i.e. the node whose depth is 0 or closest to 0). Each time, the longitudinal displacement of the node of previous depth may serve as initial value for searching the longitudinal location offset of current node, and the longitudinal offset that give rise to a maximum for the envelop cross-correlation function may be searched out in a small longitudinal search region which was set on the base of the initial value.

For the node with smallest depth, since actually this node has no "node of previous depth", the longitudinal displacement of its "node of previous depth" may be set to 0.

For the nodes with other depth, assume that the depth of current node can be t and the obtained longitudinal displacement of the node of previous depth can be $u_y$, the initial location for searching the envelope longitudinal offset of current node may be $t+u_y$. That is, the envelope longitudinal offset of current node may be obtained by setting a small longitudinal search region in the second frame which centers on the location with depth $t+u_y$ and finding the location at which the correlation between them is maximum within the longitudinal search region. The longitudinal search region may be pre-set by the imaging system. The smaller the region, the smaller the amount of calculation.

According to the second method, the calculation may start from the node with smallest depth in the ROI selected by the user. Each time, the displacement of the node of previous depth serves as initial value for searching the longitudinal location offset of current node, and the longitudinal offset that give rise to maximum for the envelop cross-correlation function may be searched out in a small longitudinal search region which was set on the base of the initial value.

For the node with smallest depth in the ROI, since the longitudinal displacement of its "node of previous depth" is unknown, it may be particularly processed. Assume that its depth can be $t_1$, when searching, a larger longitudinal search region around a longitudinal location $t_1$ in the second data frame may be set to find out a location with maximum correlation to obtain the envelop longitudinal offset. The longitudinal search region may be pre-set by the system, which may be usually larger than the search region of the guided searching (i.e. where there is initial value). If the longitudinal search region was set to be too small, the result of the search may be inaccuracy.

For the nodes with other depths, assume that the obtained displacement of the node of previous depth can be $u_y$ and the depth of current node can be t, the initial location for searching the envelope longitudinal offset of current node can be $t+u_y$. That is, the envelope longitudinal offset of current node may be obtained by setting a small longitudinal search region in the second frame of envelope data which centers on the location with depth $t+u_y$ and finding the location within the longitudinal search region at which the correlation between them is maximum, to obtain the envelope longitudinal offset of current node. The longitudinal search region may be pre-set by the system. The smaller the region, the smaller the amount of calculation. Assume that the obtained envelop longitudinal offset of current node can be $u_0$, when calculating the cross-correlation phase, the corresponding longitudinal locations of current node in the first frame and the second frame may respectively be t and $t+u_0$.

207, finding out the horizontal location for cross-correlation phase calculation;

After determining the longitudinal location, preferably, horizontal location may further be found out, that is, finding out horizontal location at which the cross-correlation function of the envelops of the two frames of data is maximum.

The searching for the horizontal location may be guided by the longitudinal locations above. That is, after obtaining the longitudinal location above, by finding out the longitudinal location in the second frame, setting a lateral search region (or search area) which centers on the longitudinal location, and calculating the lateral offset of the location within the lateral search region at which the cross-correlation of the envelop data of the two frames is maximum with respect to its original location, when subsequently calculate the cross-correlation phase, the horizontal location of the second data frame may be selected based on the lateral offset. The lateral search region may be pre-set by the system. The smaller the region, the smaller the amount of calculation. The methods for determining the correlation during searching may be SAD methods, NCC methods or other methods, similar to those for searching the longitudinal locations.

Assume that the two-dimension location of current target node in the first frame data can be (t, x), where t can be amount of time-shift and x can be the location of scanning line, and the envelop longitudinal offset obtained in last step can be $u_0$, when searching, by setting a small lateral search region which centers on location $t+u_0$ and finding out a location within this lateral search region at which the cross-correlation of the envelop data of the two frames is maximum, the lateral offset may be obtained by finding out the offset of this location with respect to its original location. Assume that the lateral offset can be $x_0$, when calculating the cross-correlation phase, the corresponding locations of the current node in the first frame and the second frame may respectively be (t, x) and ($t+u_0$, $x+x_0$).

Because the lateral displacement of tissue can be relative small and the change upon changing of depth can be small, it may not be necessary to continuously search the horizontal location above alone the nodes of each depth, but there may be an interval of few nodes to update the horizontal location. This way, the amount of calculation may be further reduced while ensuring the image quality. The interval may be pre-set by the system. If the interval was too small, the horizontal location would be updated frequently and the amount of calculation would increase. If the interval was too large, the quality of the cross-correlation estimation may be affected.

It is also possible to only search the longitudinal location but not the horizontal location. That is, the horizontal location remains unchanged. This way, the calculation may be simplified. When the actual lateral displacement of tissue is small, it will not significantly affect the quality of the cross-correlation estimation; when the actual lateral displacement of tissue is relative large, the quality of the estimation may be decreased.

209, calculating the cross-correlation phase;

After obtaining the cross-correlation phase calculation location, the cross-correlation phase estimation may be performed. The cross-correlation phase calculation may be performed using two successive frames of I/Q data. During the calculation, using the location as a center, a block of data which centers on (or is referenced on) the location may be selected for calculation, as shown in FIG. 4. The size of the block of data may be pre-set by the system. The size of the block of data may affect the result of the cross-correlation phase estimation.

The data blocks used in the calculation are referred to as kernel, which may be one-dimensional or two-dimensional. As shown in FIG. 4, assume that the location coordinate of current target point (i.e. current node) in the first frame of data can be (t, x), and the envelope longitudinal and lateral offset obtained from previous steps can respectively be $u_0$ and $x_0$, it's corresponding location coordinate in the second frame of data can be ($t+u_0$, $x+x_0$). In FIG. 4, the areas shown are obtained by longitudinally and laterally extending from the points (t, x) and ($t+u_0$, $x+x_0$) (which are as center points or reference points) by a certain distance, respectively. The data within the areas may be used as the kernel data. There may be many methods for generating the kernel from the target points in the two frames of images. The kernel may be obtained by extending from the point which is as the reference point by a certain points in all directions, or by other ways. But the methods for generating the kernel in the two frames of images may be the same. Therefore, the kernel data in the two frames of images have same size and each point used in the calculation has a corresponding point in the kernel in the other frame of image.

The phase calculation use I, Q data. Taking out the I, Q kernel data at the corresponding location in the first frame and the second frame, the phase calculated may be:

$$\varphi = \arctan\left[(-1)^n \cdot \sum_{i,j} \frac{I_2(i,j)Q_1(i,j) - I_1(i,j)Q_2(i,j)}{I_1(i,j)I_2(i,j) + Q_1(i,j)Q_2(i,j)}\right],$$

where $I_1$ and $Q_1$ are the data of the first frame, $I_2$ and $Q_2$ are the data of the second frame, and $(i, j)$ represent the relative coordinate or location of the sampling points of the kernel in the kernel. The relative location represented by same $(i, j)$ in the two frames of data are same. For example, assume that $(0, 0)$ represent the point located in the lower left corner of the kernel data in the first frame, $(0, 0)$ also represent the point located in the lower left corner of the kernel data in the second frame.

In the formula above, n may be calculated based on the displacement estimation of the node of previous depth. Assume that the longitudinal displacement of the node of previous depth can be $u_y$, then $$n = \text{round}\left(\frac{u_y}{T_c/2}\right),$$

where round represents rounding to the nearest whole number (Rounding up or rounding down may also be used).

Furthermore, since the results of the arctan function are between $$-\frac{\pi}{2} \text{ and } \frac{\pi}{2},$$

the results may be regulated into the range of $-\pi$ to $\pi$ based on the signs of the numerator and denominator of the expression:

$$(-1)^n \cdot \sum_{i,j} \frac{I_2(i,j)Q_1(i,j) - I_1(i,j)Q_2(i,j)}{I_1(i,j)I_2(i,j) + Q_1(i,j)Q_2(i,j)}.$$

According to the phase distribution of trigonometric functions, the sign of the numerator corresponds to the sin $\phi$ and the sign of the denominator corresponds to the cos $\phi$.

211, calculating the longitudinal displacement;

On the base of the calculation above, for the current node (or displacement estimation point), the longitudinal displacement of the two frames may be:

$$u'_y = nT_c/2 + \phi/\omega_c,$$

where $T_c$ is the period of the signals, which corresponds to the center angular frequency $\omega_c$ of the signals. The introduction of the $nT_c/2$ compensates the aliasing of the phase calculation, which enable present methods to be suitable for both small and large displacement conditions.

The longitudinal displacement above may be expressed in units of sampling time, or may also be expressed in units of physical length. The sampling time and the physical length have one to one correspondence.

After obtaining the longitudinal displacements at all nodes (or displacement estimation points) in the grid, the strain (i.e. the value of the strain) may be obtained by calculating the longitudinal gradient of the displacement.

During post-processing of the strain, the strain may be corrected. For example, abnormal jumping points or apparent error points may be detected and corrected; spatial smoothing may be performed to improve the display effect of the images; or, they may be mapped by different gray or color atlas to increase the contrast of the images.

Finally, the strain of a region of interesting may be output and displayed as strain images, which may reflect the difference of the elasticity of the tissue in the region of interesting.

The GPZE displacement detection methods on the one hand use the displacement of previous depth to guide the displacement calculation of current depth to reduce the amount of calculation for searching, on the other hand use phase estimation methods to calculate the displacement, therefore there is relatively low requirement on the sampling rate of original data and the amount of calculation may be significantly reduced.

At the same time, lateral searching may be introduced, therefore the quality of the estimation of the longitudinal displacement may be increased, which lead to higher signal-to-noise ratio of the images.

Furthermore, the interference resulted from phase aliasing may be compensated; therefore the application scope of the displacement estimation may be expanded.

In the embodiments above, the longitudinal location for cross-correlation phase calculation is found out first, and then the horizontal location may be found out. In fact, it is possible to find out the horizontal location first, and then find out the longitudinal location. Or, there may be no certain order between the searching for the horizontal location and for the longitudinal location, which may be performed independently. The methods for searching may be the same as the embodiments aforesaid. Specifically, for example, the methods for searching the horizontal location may be setting a lateral search region which centers on the target point and finding out the lateral offset of the location at which the cross-correlation of the envelope data of the two frames is maximum with respect to its original location, which is what needed. The methods for searching the longitudinal location may, for example, be searching the point which has maximum correlation with the kernel data in a region which centers on the sum of the location of the target point and the longitudinal displacement of previous calculation point, and the longitudinal location of this point being the longitudinal location for cross-correlation phase calculation of the target point in the second frame image.

Figure 5:
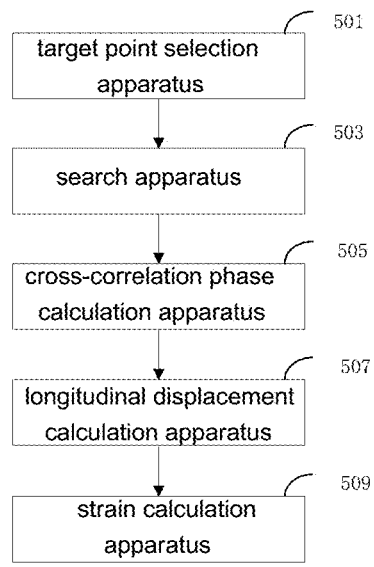
FIG. 5 is a block diagram of a device for detecting displacement in elastography according to an embodiment of the present disclosure.

As shown in FIG. 5, an embodiment of present disclosure further provides a device for detecting displacement in elastography, which may include:

a target point selection apparatus 501 that can select the target point;

a search apparatus 503 that can obtain the cross-correlation phase calculation location of the target point in the second frame image;

a cross-correlation phase calculation apparatus 505 that can calculate the cross-correlation phase based on the cross-correlation phase calculation location;

a longitudinal displacement calculation apparatus 507 that can calculate the longitudinal displacement based on the cross-correlation phase;

a strain calculation apparatus 509 that can determine the strain by calculating the gradient of the displacement.

In an embodiment, the device may further include:

baseband signal acquiring apparatus that can acquire the baseband signal;

gridization apparatus that can grid the baseband signal. The nodes of the grid may serve as displacement estimation points, and the target point may be the displacement estimation points.

In an embodiment, the cross-correlation phase calculation location of the target point in the second frame image may include the longitudinal location for cross-correlation phase calculation.

In some embodiment, the searching apparatus can:

obtain the longitudinal displacement of the previous calculation point of the target point, and search the point which has maximum correlation with the kernel data within the region which centers on the sum of the location of the target point and the longitudinal displacement of the previous calculation point in the second frame image, where the longitudinal location of this point can be the longitudinal location for the cross-correlation phase calculation of the target point in the second frame image.

In an embodiment, the cross-correlation phase calculation location of the target point in the second frame image may include the horizontal location for the cross-correlation phase calculation.

The searching apparatus can further:

laterally search the point which has maximum data correlation in the vicinity of the longitudinal location for the cross-correlation phase calculation, where the horizontal location of this point is the horizontal location for the cross-correlation phase calculation.

In an embodiment, the search apparatus may laterally search the point which has maximum data correlation in the vicinity of the longitudinal location for the cross-correlation phase calculation once every few points.

In an embodiment, the cross-correlation phase calculating apparatus can: obtain first kernel and second kernel which center on the location of the target point in the first frame and on the cross-correlation phase calculation location of the target point in the second frame, respectively.

The cross-correlation phase $\varphi$ may be:

$$\varphi = \arctan\left[(-1)^n \cdot \sum_{i,j} \frac{I_2(i,j)Q_1(i,j) - I_1(i,j)Q_2(i,j)}{I_1(i,j)I_2(i,j) + Q_1(i,j)Q_2(i,j)}\right],$$

where $I_1$ and $Q_1$ are the data of the first frame, $I_2$ and $Q_2$ are the data of the second frame, and (i, j) represent the relative location of the sampling point of the kernel in the kernel; where $$n = \text{round}\left(\frac{u_y}{T_c/2}\right),$$

where $T_c$ is the period of the signals, which correspond to the center frequency $\omega_c$, and $u_y$ is longitudinal displacement of the previous calculation point.

In an embodiment, specifically, the longitudinal displacement calculation apparatus can calculate:

$$u'_y = \frac{nTc}{2} + \frac{\varphi}{\omega_c},$$

where $u'_y$ is the longitudinal displacement, and $\varphi$ is the cross-correlation phase.

In an embodiment, the device may further include:
correction apparatus that can correct the strain acquired;
or
smooth apparatus that can spatial smooth the strain;
or
map apparatus that can map the strain with different gray or color atlas.

The methods and apparatuses for elastography may be provided by embodiments of present disclosure. By obtaining two frames of down sampled I/Q baseband echo signals, detecting rapidly the displacement between the two frames using the guided phase zero estimation (GPZE) method, and determining the strain by calculating the axial gradient the methods and devices described herein may not only provide strain images with high quality, but also reduce the amount of calculation, thereby meeting clinical requirement in real time.

Above are detailed description of present disclosure made with reference to specific embodiments, which should not be considered as that the specific embodiments of present disclosure are limited to the description. Many simple derivations and replacements may be made by an ordinary skilled person in the art without departing from the concept of present disclosure, which should be considered as being within the scope of present disclosure.

What is claimed is:

1. A method for detecting displacement in elastography within an ultrasound imaging system, comprising:
acquiring at least two successive frame images from ultrasound signals using an ultrasound probe;
selecting a target point in a first frame image;
obtaining a cross-correlation phase calculation location of the target point in a second frame image;
calculating a cross-correlation phase based on the cross-correlation phase calculation location; and
calculating a longitudinal displacement based on the cross-correlation phase;
wherein the cross-correlation phase calculation location comprises a longitudinal location for cross-correlation phase calculation; and
wherein obtaining a cross-correlation phase calculation location of the target point in a second frame image comprises:
determining a longitudinal displacement of a previous calculation point of the target point;
in the second frame image, searching a point which has maximum correlation with kernel data within a region which centers on a sum of location of the target point and the longitudinal displacement of the previous calculation point, wherein longitudinal location of the point which has maximum correlation with kernel data serves as the longitudinal location for the cross-correlation phase calculation of the target point in the second frame image.

2. The method of claim 1, wherein before selecting the target point, further comprising:
acquiring baseband signal data;
gridizing the baseband signal data, wherein grid nodes serve as displacement estimation points;
wherein the target point is selected from the displacement estimation points.

3. The method of claim 1, wherein:
the cross-correlation phase calculation location further comprises horizontal location for cross-correlation phase calculation;
obtaining a cross-correlation phase calculation location of the target point in a second frame image further comprises:
laterally searching a point which has maximum data correlation in the vicinity of the longitudinal location for the cross-correlation phase calculation, wherein a lateral location of the point of maximum data correlation in the vicinity of the longitudinal correlation serves as the horizontal location for the cross-correlation phase calculation.

4. The method of claim 3, wherein:
laterally searching a point which has maximum data correlation in the vicinity of the longitudinal location for the cross-correlation phase calculation is performed once every few points.

5. The method of claim 1, wherein:
calculating a cross-correlation phase based on the cross-correlation phase calculation location comprises:
obtaining a first kernel and a second kernel which center on location of the target point in the first frame image and on the cross-correlation phase calculation location of the target point in the second frame image, respectively,
wherein the cross-correlation phase $\varphi$ is:

$$\varphi = \arctan\left[(-1)^n \cdot \sum_{i,j} \frac{I_2(i,j)Q_1(i,j) - I_1(i,j)Q_2(i,j)}{I_1(i,j)I_2(i,j) + Q_1(i,j)Q_2(i,j)}\right],$$

wherein $I_1$ and $Q_1$ are data of the first frame, $I_2$ and $Q_2$ are data of the second frame, and (i, j) represent a relative location of a sampling point of a kernel;
wherein $$n = \text{round}\left(\frac{u_y}{T_c/2}\right),$$

wherein $T_c$ is a period of the signals, which corresponds to a center frequency $\omega_c$, and $u_y$ is the longitudinal displacement of the previous calculation point.

6. The method of claim 5, wherein:
calculating a longitudinal displacement based on the cross-correlation phase comprises:

$$\text{calculating } u'_y = \frac{nTc}{2} + \frac{\varphi}{\omega_c},$$

wherein $u'_y$ is the longitudinal displacement, and $\varphi$ is the cross-correlation phase.

7. A method for detecting displacement in elastography within an ultrasound imaging system, comprising:
acquiring at least two successive frame images from ultrasound signals using an ultrasound probe;
selecting a target point in a first frame image;
obtaining a cross-correlation phase calculation location of the target point in a second frame image;
calculating a cross-correlation phase based on the cross-correlation phase calculation location; and
calculating a longitudinal displacement based on the cross-correlation phase;
wherein the cross-correlation phase calculation location comprises a longitudinal location for the cross-correlation phase calculation and horizontal location for the cross-correlation phase calculation;
and wherein obtaining a cross-correlation phase calculation location of the target point in a second frame image comprise:
in the second frame image, searching a point at which cross-correlation of envelope data of the first frame image and second frame image is maximum in a pre-set lateral search region which centers on the target point, wherein lateral location of said point serves as the horizontal location for the cross-correlation phase calculation;
in the second frame image, searching a point which has maximum correlation with kernel data in a region which centers on a sum of the location of the target point and the longitudinal displacement of a previous calculation point of the target point, wherein longitudinal location of the point which has maximum correlation with kernel data serves as the longitudinal location for the cross-correlation phase calculation of the target point in the second frame image.

* * * * *